(12) United States Patent
Feulner et al.

(10) Patent No.: US 10,049,522 B2
(45) Date of Patent: Aug. 14, 2018

(54) METHOD AND DEVICE FOR EXAMINING VALUE DOCUMENTS FOR IRREGULARITIES

(71) Applicant: GIESECKE & DEVRIENT GMBH, München (DE)

(72) Inventors: Johannes Feulner, München (DE); Jan Domke, Vaterstetten (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 137 days.

(21) Appl. No.: 15/021,798

(22) PCT Filed: Sep. 11, 2014

(86) PCT No.: PCT/EP2014/002465
§ 371 (c)(1),
(2) Date: Mar. 14, 2016

(87) PCT Pub. No.: WO2015/036120
PCT Pub. Date: Mar. 19, 2015

(65) Prior Publication Data
US 2016/0232731 A1 Aug. 11, 2016

(30) Foreign Application Priority Data
Sep. 13, 2013 (DE) .......................... 10 2013 015 224

(51) Int. Cl.
*G07D 7/08* (2006.01)
*G01N 29/09* (2006.01)
(Continued)

(52) U.S. Cl.
CPC .............. *G07D 7/08* (2013.01); *G01N 29/04* (2013.01); *G01N 29/11* (2013.01); *G07D 7/182* (2013.01); *G07D 7/183* (2017.05)

(58) Field of Classification Search
CPC ............ G01D 7/08; G01D 7/06; G01D 7/004; G01N 29/04; G01N 29/07; G01N 29/11; G01N 29/12; G01N 29/46; G01N 29/4454
See application file for complete search history.

(56) References Cited

U.S. PATENT DOCUMENTS 6,040,584 A * 3/2000 Liu ........................ G01N 21/88
194/207
6,595,060 B2 * 7/2003 Wunderer .............. G01N 29/07
73/159

(Continued)

FOREIGN PATENT DOCUMENTS

CN 1729488 A 2/2006
CN 1853202 A 10/2006
(Continued)

OTHER PUBLICATIONS

Gnanadesikan, R., et. al., "Robust Estimates, Residuals, and Outlier Detection with Multiresponse Data," Biometrics, Mar. 1, 1972, pp. 81-124, vol. 28 No. 1.
(Continued)

*Primary Examiner* — Helen Kwok
(74) *Attorney, Agent, or Firm* — Justin J. Cassell; Workman Nydegger

(57) ABSTRACT

A means and method for checking a value document of at least one irregularity of at least one specified type, in which an ultrasound data record is captured which describes in locally resolved fashion at least one ultrasound property, a deviation data record is ascertained which describes in locally resolved fashion a deviation between the ultrasound data record and a model and is ascertained such that the deviation described thereby is minimal with respect to the model. The model comprises a model for the location dependence of the at least one ultrasound property of reference value documents of the specified value document (Continued)

type without irregularities of the at least one specified type, and using the deviation data record, it is checked whether an indication of an irregularity of the at least one type is present on the value document.

24 Claims, 5 Drawing Sheets

(51) Int. Cl.
  *G01N 29/04* (2006.01)
  *G01N 29/11* (2006.01)
  *G07D 7/182* (2016.01)
  *G07D 7/183* (2016.01)

(56) References Cited

U.S. PATENT DOCUMENTS

| | | | |
|---|---|---|---|
| 7,571,796 B2 | 8/2009 | Stenzel et al. | |
| 7,607,528 B2 | 10/2009 | Derks et al. | |
| 8,464,587 B2 | 6/2013 | Domke et al. | |
| 8,510,062 B2 * | 8/2013 | Domke | G01N 29/0618 702/189 |
| 8,766,222 B2 | 7/2014 | Wunderer et al. | |
| 9,165,336 B2 * | 10/2015 | Scholz | G07D 7/08 |
| 9,418,499 B2 * | 8/2016 | Rauscher | G07D 7/122 |
| 9,582,953 B2 * | 2/2017 | Feulner | G07D 11/0078 |
| 9,600,952 B2 * | 3/2017 | Domke | G07D 7/08 |
| 9,683,972 B2 * | 6/2017 | Domke | G01N 29/36 |
| 9,792,750 B2 * | 10/2017 | Domke | G07D 7/08 |
| 2003/0025512 A1 * | 2/2003 | Wunderer | G01N 29/11 324/639 |
| 2006/0151282 A1 | 7/2006 | Derks et al. | |
| 2007/0187209 A1 | 8/2007 | Stenzel et al. | |
| 2009/0312957 A1 | 12/2009 | Domke et al. | |
| 2010/0005888 A1 | 1/2010 | Domke et al. | |
| 2010/0060881 A1 * | 3/2010 | Kayani | G01N 21/8914 356/72 |
| 2011/0226061 A1 * | 9/2011 | Itsumi | B65H 7/02 73/589 |
| 2011/0231009 A1 | 9/2011 | Yamamoto et al. | |
| 2011/0255750 A1 | 10/2011 | Wunderer et al. | |
| 2014/0125968 A1 | 5/2014 | Rauscher et al. | |
| 2014/0352441 A1 | 12/2014 | Domke et al. | |
| 2017/0061638 A1 * | 3/2017 | Schmalz | G07D 7/20 |

FOREIGN PATENT DOCUMENTS

| | | |
|---|---|---|
| CN | 101536044 A | 9/2009 |
| CN | 101788280 A | 7/2010 |
| CN | 102194274 A | 9/2011 |
| CN | 102265312 A | 11/2011 |
| CN | 102542656 A | 7/2012 |
| DE | 10 2006 033 * | 1/2008 |
| DE | 102006033001 A1 | 1/2008 |
| DE | 102009058439 A1 | 6/2011 |
| DE | 102011016509 A1 | 10/2012 |
| DE | 102011121912 A1 | 6/2013 |
| WO | 2008009384 A1 | 1/2008 |

OTHER PUBLICATIONS

Platt John C., "Probabilistic Outputs for Support Vector Machines and Comparisons to Regularized Likelihood Methods," Advances in Large Margin Classifiers, Mar. 26, 1999, 11 pages.
Hendrch, Norman, "Principal Component Analysis VL Algorithmisches Lernen, Teil 3a," Jun. 23, 2010, University at Hamburg, 60 pages, URL: http://tams-www.informatik.uni-hamburg.de/lehre/2010ss/vorlesung/Algorithmisches_Lemen/folien/pca.pdf.
German Search Report from Corresponding German Application No. DE 10 2013 015 224.0. dated Mar. 19, 2014.
International Search Report from Corresponding PCT Application No. PCT/EP2014/002465, dated Jan. 23, 2015.
International Preliminary Report on Patentability from Corresponding PCT Application No. PCT/EP2014/002465, dated Mar. 15, 2016.
Chinese Office Action from CN Application No. CN 201480049369.X, dated Nov. 3, 2017.

* cited by examiner

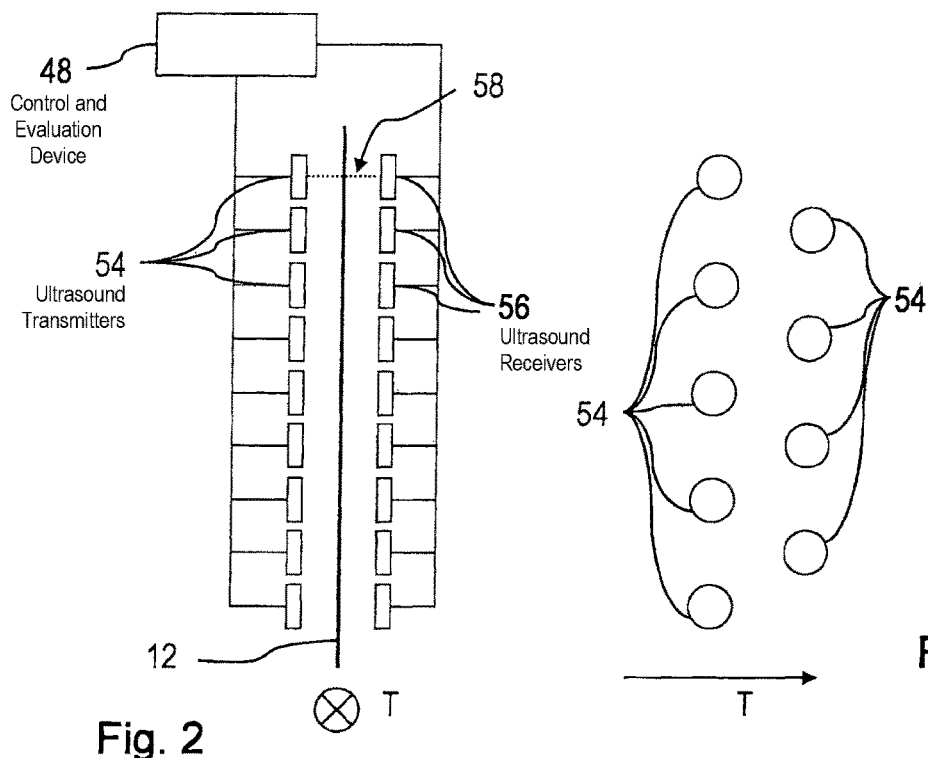
Fig. 2
Fig. 3
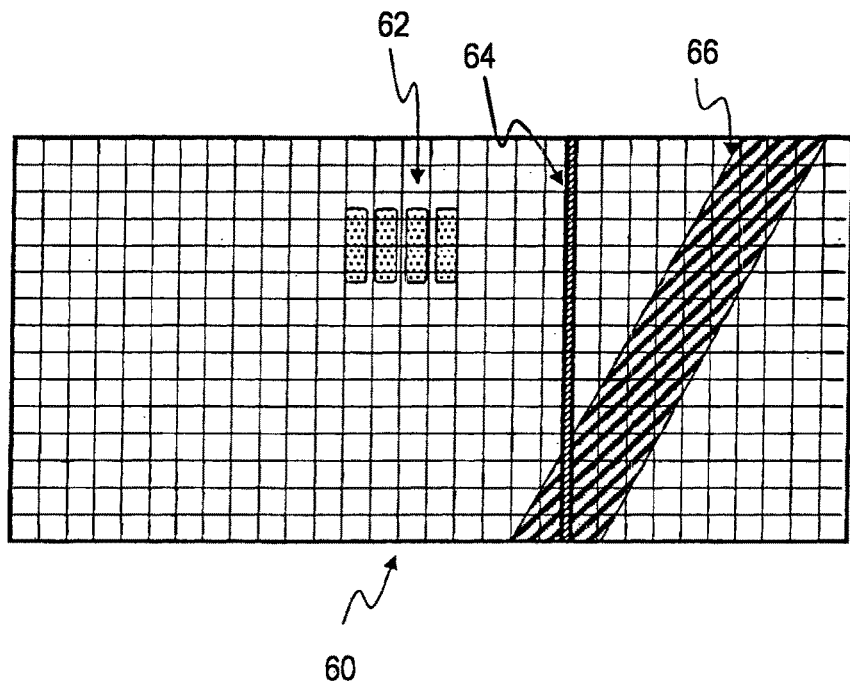
Fig. 4

METHOD AND DEVICE FOR EXAMINING VALUE DOCUMENTS FOR IRREGULARITIES

BACKGROUND

The present invention relates to a method for checking a value document of a specified value document type for the presence of at least one irregularity of at least one specified type, preferably at least one adhesion, preferably an adhesive strip, and/or at least one crease and/or a material removal, and means for carrying out the method.

In this context, value documents are understood to mean sheet-shaped objects, which represent for example a monetary value or an authorization and thus shall not be manufacturable at will by unauthorized persons. Hence, they have features that are not easily produced, in particular copied, whose presence is an indication of authenticity, i.e. of production by an authorized body. Important examples of such value documents are coupons, vouchers, checks and in particular bank notes.

Such value documents may have irregularities or defects which may make them appear unsuitable for a future usage or even are to be regarded as a, perhaps only weak, suspicion on the presence of a forgery.

An example of lacking suitability for a future usage can be, for example, the presence of an adhesive strip on a value document, in particular a bank note. Such adhesive strips are often employed to repair tears in the respective value document. The damaged value document should hence be withdrawn from circulation, if possible. Another example may be that, in polymer bank notes, regions of an opaque layer applied on the polymer substrate before or on printing chip off in the course of time, so that a material removal is the result.

However, adhesive strips may also be used to connect parts of different value documents with each other to produce a forgery.

For recognizing adhesive strips, a value document may be examined, for example, by means of ultrasound transmission. With the aid of the measuring data there can then be checked whether an indication of the presence of an adhesive strip can be recognized.

A further form of irregularities which may impair the bank notes' fitness for circulation are creases and wrinkles. In U.S. Pat. No. 6,595,060B2 there is described, for example, a method for the determination of structural inhomogeneities in sheet material, in particular due to wrinkles or tears, in which ultrasound is employed. In the following, creases are understood to also be wrinkles.

However, such known methods suffer from the ultrasound transmission data being very noisy, which is due to the kind of measurement and the properties of certain types of value documents, and the recognition of adhesive strips or creases or material removals thus being possibly difficult. Likewise, the local resolution is substantially lower than with optical examinations.

SUMMARY

The present invention is hence based on the object of stating a method for checking a value document of a specified value document type for the presence of at least one irregularity of at least one specified type, preferably an adhesion, particularly preferably an adhesive strip, and/or a crease and/or an irregularity in the form of at least one material removal, which allows a good recognition of such irregularities, and providing means for carrying out the method.

In particular, the object is achieved by a method for checking a value document of a specified value document type for the presence of at least one irregularity of at least one specified type, in which an ultrasound data record is captured which describes in locally resolved fashion at least one ultrasound property, preferably the ultrasound transmission of the value document. A deviation data record is ascertained which describes in locally resolved fashion a deviation between the ultrasound data record and a model and is ascertained such that the deviation described thereby is minimal with respect to the model, the model comprising a model for the location dependence of the at least one ultrasound property of reference value documents of the specified value document type without irregularities of the at least one specified type. Using the deviation data record, it is checked whether an indication of an irregularity of the at least one specified type is present on the value document.

The object is further achieved by an apparatus for checking a value document of a specified value document type for the presence of at least one irregularity of at least one specified type with an evaluation device which is configured to execute a method according to the invention. It is in particular configured to capture an ultrasound data record which describes in locally resolved fashion at least one ultrasound property, preferably the ultrasound transmission, of the value document, to ascertain a deviation data record which describes in locally resolved fashion a deviation between the ultrasound data record and a model and is ascertained such that the deviation described thereby is minimal with respect to the model, the model comprising a model for the location dependence of the at least one ultrasound property of reference value documents of the specified value document type without irregularities of the at least one specified type, and, using the deviation data record, to check whether an indication of an irregularity of the specified type is present on the value document.

For carrying out the method, the apparatus has the evaluation device. This may have a data processing device which, for example, may have a computer or at least one processor and/or at least one FPGA for processing the ultrasound data. The evaluation device may have a memory in which a computer program is stored, so that the evaluation device, preferably the data processing device executes the method according to the invention upon the execution of the computer program.

The object is hence also achieved by a computer program for execution by means of a data processing device, which has program code, upon the execution of which the data processing device executes a method according to the invention.

The object is further achieved by a physical data carrier which is readable by means of a data processing device and on which a computer program according to the invention is stored.

The method and the apparatus relate to the check of a value document of a specified value document type. The value document types may be given in that in each case different models within the meaning of the invention are necessary for them. In the case of value documents in the form of bank notes, a value document type may be given in particular by the currency and the face value or denomination and, where applicable, the series or issue. The value document type of bank notes may also be determined in more detail with respect to the subsequent processing, namely by the orientation of the bank notes. The orientation here is understood to mean one of the four possible positions of the bank note upon the capture of the ultrasound property, which positions may transition into each other by a rotation around the longitudinal center axis and/or transverse center axis of the bank note.

The value documents are checked for the presence of at least one irregularity of at least one specified type. The reference value documents preferably do not have irregularities of the at least one specified type which is checked.

An irregularity of at least one specified type is understood to mean, depending on the embodiment, an irregularity of only one specified type or an irregularity of one of several specified types. In particular, the following types may be considered alone or in combination.

Thus, irregularities of the at least one specified type may comprise irregularities of the type of an adhesion, preferably an adhesive strip and/or irregularities of the crease type. The type of the irregularity may thus preferably be an adhesion, preferably an adhesive strip. Adhesions are understood to mean any elements which are connected with the value document and are arranged at least partially on its surface. These may be, for example, regions with an ink of enough weight per unit area or in particular also adhesive strips or other adhesive elements glued onto the value document. Irregularities of this type are also referred to as irregularities in the form of adhesions. The type of the irregularity may thus preferably also be a crease. A crease within the framework of the invention is understood to mean only such a crease which leads to a change of the ultrasound property recognizable by a sensor. Irregularities of this type are also referred to as irregularities in the form of creases.

Irregularities of the adhesion and/or crease types are irregularities in the form of adhesions and/or creases.

The type of the irregularity may preferably also be a material removal. The irregularity of this type is also be referred to as irregularity in the form of a material removal. Material removals within the framework of the present invention are value document regions whose weight per unit area is reduced compared with corresponding regions of specified reference value documents of the specified value document type. In particular in the case of value documents having a polymer layer with an opaque layer applied thereon these regions can be regions in which the opaque layer is damaged, in particular is no longer present.

Preferably, the check is effected either only for the presence of at least one irregularity in the form of an adhesion and/or a crease or only for the presence of at least one irregularity in the form of a material removal. In the first case, the reference value documents then preferably merely need not have any irregularities in the form of adhesive strips and creases, in the second case merely not any irregularities in the form of material removals. Particularly preferably, the check either is only effected for the presence of at least one irregularity in the form of an adhesion or only for the presence of at least one irregularity in the form of a crease or only for the presence of at least one irregularity in the form of a material removal. In the first case, the reference value documents then preferably merely need not have any irregularities in the form of adhesive strips, in the second case merely not any irregularities in the form of creases and in the third case merely not any irregularities in the form of material removals.

For the check, an ultrasound data record is captured, which describes in locally resolved fashion at least one ultrasound property of the value document. The ultrasound property may be, for example, phase changes upon remission and/or transmission of ultrasound at or through the value document or preferably the remissivity or the remission or remission intensity or remission amplitude for ultrasound in a specified frequency region or the transmissivity or the transmission or transmission intensity or transmission amplitude for ultrasound in a specified frequency region. Ultrasound is understood here to mean sound with frequencies in a region between 50 kHz and 2 MHz, preferably between 50 kHz and 1 MHz, particularly preferably between 100 kHz and 1 MHz. Very particularly preferably, ultrasound with frequencies in the region between 100 kHz and 500 kHz is employed.

The ultrasound data record describes the ultrasound property in locally resolved fashion, that is, that for a plurality of measuring dots on the value document there are given ultrasound data corresponding to the respective place of the measuring dot and describing the ultrasound property. The places may be explicitly indicated in the ultrasound data record here. However, it is also possible that the place is implicitly given by the arrangement of the ultrasound data in the ultrasound data record; in this case a rule is specified as to which places correspond to which ultrasound data in the ultrasound data record. Preferably, ultrasound data are captured for places which are distributed over the whole value document. The places may be distributed irregularly, but preferably they are distributed regularly, particularly preferably on the node of a rectangle grid.

In principle, it is sufficient that the ultrasound data record is merely captured, for example read or received. The apparatus, preferably the evaluation device, may have, for this purpose, a suitable interface via which ultrasound data records can be captured.

However, in the method, the ultrasound data are preferably captured by means of an ultrasound sensor. In the apparatus it is then preferred, that the apparatus further has an ultrasound sensor for the locally resolved measurement of the at least one ultrasound property of a value document and formation of an ultrasound data record for the value document, and that the evaluation device is coupled to the ultrasound sensor via a signal connection and is configured to capture an ultrasound data record of the ultrasound sensor as an ultrasound data record.

The ultrasound sensor may be configured for measuring the ultrasound property of a value document which is at rest relative to the ultrasound sensor. However, it is preferred that the ultrasound sensor is configured such that it measures the ultrasound property of the value document during a motion of the value document, in particular during a transport of the value document past or through the ultrasound sensor. For this purpose, a transport device may be provided which transports the value document at a specified transport speed past or through the ultrasound sensor.

The ultrasound sensor may preferably have several ultrasound transducers which may serve as ultrasound transmitters and/or ultrasound receivers. In particular, the ultrasound sensor may be a transmission ultrasound sensor. Upon the formation of the ultrasound data record, the measuring signals of the ultrasound transducers acting as ultrasound receivers may be subjected to a preprocessing.

The captured ultrasound data record is then compared to the model. More precisely, from the captured ultrasound data record there is ascertained the deviation data record which describes in locally resolved fashion a deviation between the captured ultrasound data record and the model. For this purpose, for the value document type there is specified the model which comprises or is a model for the location dependence of the at least one ultrasound property of reference value documents of the specified type without irregularities of the at least one specified type, preferably depending on the at least one specified type without adhesions and/or creases and/or material removals. The model hence describes approximatively the at least one ultrasound property of the reference value documents in locally resolved fashion. The model describes the location dependence of the ultrasound property or the location-dependent ultrasound property of the reference value documents by way of a model, thus need not render the location dependence of the ultrasound property exactly, but, as the term "model" implies, only approximatively, i.e. with certain errors. The errors, however, as the term "model" implies, may not become arbitrarily large. The person skilled in the art chooses the allowed error or accuracy of the model in such a way that the method according to the invention works in such a way that it meets the requirements in particular in view of embodiment speed and recognition accuracy.

In a simple case, the model needs to define only one model data record which is obtainable, for example, by an averaging of reference ultrasound data records for value documents of the specified value document type without irregularities of the at least one specified type, preferably depending on the at least one specified type without in the form of adhesions and/or creases and/or material removals.

In the method it is preferred, however, that the model defines a plurality of model data records differing from each other, which describe the at least one ultrasound property in location-dependent fashion. In the apparatus it is accordingly preferred that the model defines a plurality of model data records differing from each other, which describe the at least one ultrasound property in location-dependent fashion. In this way, there can be modelled particularly well variations in the ultrasound properties of the value documents of the specified value document type, which are caused by the value document type and/or the manufacturing, but not by later attached adhesions or later generated creases or later effected material removals. This may substantially increase the selectivity of the method.

The model may be specified by the model data records being explicitly specified. Preferably, however, the model is specified by model parameters and an instruction for ascertaining model data records using the model parameters being at least given such that the deviation data record can be ascertained.

The deviation data record is ascertained such that the deviation with respect to the model, i.e. from the model, described thereby, is minimal. For ascertaining the quantity of a deviation between an ultrasound data record and the model, a deviation measure can be specified which is chosen in dependence on the model and the representation of the ultrasound data records. A deviation is minimal when the deviation measure is minimal. Preferably, the deviation between the ultrasound data record and the model is a deviation between the ultrasound data record and one of the model data records.

This deviation data record will include deviations, besides the deviations which may occur between the model and value documents without irregularities due to the usage of the model, which are caused by irregularities of the at least one specified type, preferably adhesions and/or creases and/or material removals. By using a model which describes the location dependence of the ultrasound property deviations are more clearly recognizable due to irregularities of the at least one specified type, preferably adhesions and/or creases and/or material removals. In particular when for reference value documents there is employed a model which defines a plurality of model data records, variations of the ultrasound property caused by fluctuations in the properties of value documents of the specified value document type, in the case of bank notes, for example, the position of watermarks and/or security threads, can be separated from such caused by adhesions or creases or material removals. This facilitates the check in the subsequent step.

Therein, using the deviation data record, it is checked whether or not an indication of an irregularity of the at least one specified type, preferably in the form of at least one adhesion, preferably an adhesive strip, and/or a crease and/or at least one irregularity in the form of a material removal, is present on the value document. In this way, a very high accuracy or reliability of the recognition of irregularities of the at least one specified type, preferably adhesions and/or creases and/or of material removals, may be achieved, even when the influence of the respective irregularities, for example adhesions or creases or of the material removals on the at least one ultrasound property, is not very large. There also results a very high reliability in the recognition.

As a result of the check, a datum may be stored or a signal be formed, which describes whether or not the mentioned indication is present. Such a datum or signal may be employed directly or, optionally, in connection with other data and/or signals describing indications of the presence of other irregularities, for sorting the value document.

In principle, the model data records do not need to be structured or defined like the ultrasound data records, as long as the deviation measure allows ascertaining a minimal deviation. Preferably, however, the ultrasound data records respectively include ultrasound data for a number N of places which is specified for the value document type, which data respectively describe the at least one ultrasound property for the respective places. Accordingly and preferably, the model data records then respectively include model data for the at least one ultrasound property for the specified number N of places. This permits a simple comparison of the ultrasound data and the model data for every place. This allows in particular a simple formulation of a distance measure, for example, as a sum of the squared differences between the ultrasound data and the model data over the given places. When representing the ultrasound data records and the model data records by vectors, the deviation measure may be given, for example, by the Euclidean or L2 norm of the difference vector which is given by the difference from the vector representing the ultrasound data record and the vector describing the model data record.

Preferably, in the method, the ultrasound data records respectively include ultrasound data for a number N of places which is specified for the value document type, which data respectively describe the at least one ultrasound property for the respective places, and the model data records respectively include model data for the at least one ultrasound property for the specified number N of places. Accordingly, in the apparatus, preferably the ultrasound data records respectively include ultrasound data for a number N of places which is specified for the value document type, which data respectively describe the at least one ultrasound property for the respective places, and the model data records respectively include model data for the at least one ultrasound property for the specified number N of places. The model data records then lie preferably in a specified partial region of an N-dimensional space of possible ultrasound data. Such a model thus provides a very large number of model data records. In addition, the model data records may form a continuum, which may greatly simplify the ascertainment of the deviation data record, because the results of minimization methods can be employed.

Preferably, in the method, the partial region is specified such that model data records are representable, in case the ultrasound data record and the model data records are represented as vectors of the same dimension, by a sum of a mean vector and a linear combination of at least five, preferably ten, specified partial-region vectors. Accordingly, in the apparatus, preferably the partial region can be specified such that model data records are representable, in case the ultrasound data record and the model data records are represented as vectors of the same dimension, by a sum of a mean vector and a linear combination of at least five, preferably ten, specified partial-region vectors. With this representation, the same components of the vector for the ultrasound data record and for the model data record respectively correspond to the same place. Furthermore, the partial-region vectors are linearly independent. This embodiment has—inter alia—the advantage that for deviation criteria like the length or norm of the difference of the vectors corresponding to the ultrasound data record or to the model data record, the deviation data record can be easily ascertained with minimal deviation without the execution of numerical minimization methods.

Preferably, the partial-region vectors are chosen such that they are orthogonal to each other.

Furthermore, preferably the mean vector and the partial-region vectors are obtainable or preferably obtained by an analysis of reference ultrasound data records for specified reference value documents of the specified value document type without irregularities of the at least one specified type, i.e. preferably depending on the at least one specified type without adhesions or creases and material removals. As reference value documents of the specified value document type there are preferably employed reference value documents of different states, for example, freshly printed and used, preferably multiply circulated value documents.

Particularly preferably, the analysis comprises a main component analysis, the mean value ascertained upon the main component analysis corresponding to the mean vector and the main components ascertained upon the main component analysis corresponding to the partial-region vectors. In this way, there can be obtained in a simple and systematic manner a model which describes the most important variations of the location-dependent ultrasound property but remains relatively simple. The person skilled in the art can chose the number of the employed partial-region vectors or main components in dependence on the properties of the value documents of the specified value document type, the resources available for carrying out the method, and the required execution speed.

Furthermore, it is preferred that the model has a statistical model distribution which describes a probability for the model data records. In particular, in case the main component analysis is employed, the statistical model distribution may correspond to a main components' distribution ascertained according to the main component analysis. The distribution is understood here to mean the probability density. This can be employed, where applicable, in the following method step.

The check whether an indication of an irregularity of the at least one specified type, preferably of an irregularity in the form of at least one adhesion, preferably an adhesive strip, and/or at least one crease and/or at least one irregularity in the form of at least one material removal, is present on the value document, may basically be carried out arbitrarily, but in a suitable manner using the deviation data record. Upon the check there may be employed parameters, which may be gained by checking training value documents of the specified value document type without irregularities of the at least one specified type, preferably in the form of at least one adhesion, for example an adhesive strip, and/or at least one crease and/or without irregularities in the form of at least one material removal, and those having such irregularities of the at least one specified type, or the use of the ultrasound training data records captured for such training value documents.

However, preferably, for the deviation data record there is ascertained, using the deviation data record, at least one feature, and upon checking whether an indication of an irregularity of the at least one specified type, preferably an irregularity in the form of at least one adhesion, preferably an adhesive strip, and/or at least one crease and/or an irregularity in the form of at least one material removal is present on the value document, the at least one feature is employed. The at least one feature is a feature representable by a feature function at least of some data of the deviation data record, so that with an irregularity of the at least one specified type, preferably an irregularity in the form of an adhesion, preferably an adhesive strip, and/or a crease and/or an irregularity in the form of a material removal, the feature function assumes a significant value. Preferably, several different such features are ascertained and employed upon the checking.

The choice of the features is only limited by their suitability for checking. In particular, preferably the following alternatives may be employed.

According to a preferred alternative, the feature or one of the features may relate to or describe the probability that the captured ultrasound data record or the deviation data record or the model data record corresponding to the deviation data record occurs according to the model. In the two first cases, the probability corresponds to the probability that the ultrasound data record corresponds to a value document of the specified value document type without irregularities of the at least one specified type, preferably depending on the at least one specified type without irregularities in the form of at least one adhesion or crease or without irregularities in the form of at least one material removal; in the last case, when employing the probability of the model data record, the probability may correspond to the probability that the ultrasound data record occurs under the condition that the value document has no irregularity of the at least one specified type, preferably, depending on the at least one specified type, no irregularity in the form of at least one adhesion, for example an adhesive strip, or one crease or no irregularity in the form of at least one material removal.

According to a further preferred alternative, the feature or one of the features may describe or represent the quantity of the deviation described by the deviation data record. The quantity is understood here to mean the whole quantity of the deviation, where applicable, normalized to for example the number of the ultrasound data of the ultrasound data records. With a representation as a vector, as a measure for the quantity there can be employed, for example, the norm or length or a function of these quantities.

According to another preferred alternative, the feature or one of the features may represent a measure for the magnitude of the deviations at those places at which the deviation data of the deviation data record indicate an irregularity of the at least one specified type, preferably depending on the at least one specified type either in the form of at least one adhesion and/or a crease or to an irregularity in the form of at least one material removal. The magnitude of the deviations may be given, for example, by the mean value and/or the variance of the deviations, which indicate the mentioned irregularity. The magnitude is ascertained for the feature in dependence on the at least one specified type, preferably either for irregularities in the form of at least one adhesion and/or a crease or for irregularities in the form of at least one material removal, because the respective deviation data may have different signs. Thus, an adhesion typically reduces the ultrasound transmission, so that depending on the representation of the deviation data record, the deviation given by the model data record or the deviation datum for a place with adhesion will be smaller than the respective captured ultrasound transmission for the same place; the deviation datum for the place is then smaller than zero. The same applies to creases. With a material removal, however, the relations are vice versa, there results the opposite sign for the deviation datum.

According to a still further alternative, the feature or one of the features may relate to or represent or describe a measure for places, for which the deviation data of the deviation data record indicate an irregularity of the at least one specified type, preferably an irregularity in the form of either at least one adhesion and/or a crease or an irregularity of at least one material removal, occurring spatially cumulated and preferably neighboring, and that preferably upon ascertaining the measure also the quantities of the deviations are taken into account. The measure may in particular depend on an energy function. An energy function is preferably understood here to mean a function which comprises a sum of contributions which respectively include products of deviation data at different places, weighted with a weighting factor depending on the distance of the places; in doing so, there are taken into account preferably only deviation data which indicate an irregularity of the at least one specified type, preferably an irregularity in the form of either at least one adhesion, preferably an adhesive strip, and/or a crease or an irregularity in the form of a material removal. In this manner, there can be taken into account whether the deviations are present only sporadically scattered and, hence, rather indicate measurement errors or whether the deviations are distributed extensively, as it is to be expected for irregularities of the at least one specified type, preferably irregularities in the form of adhesions and/or creases or material removals.

A still further preferred alternative relates in particular to the case that the irregularities of the at least one specified type, for example irregularities in the form of adhesions and/or creases or of material removals, typically have a specified form, for example in the case of adhesive strips are strip-shaped and straight. In the method, preferably the feature or one of the features may relate to or represent a measure for the presence of deviations at places for which the deviation data of the deviation data record indicate an irregularity of the at least one specified type, for example an irregularity in the form of an adhesion and/or crease or an irregularity in the form of a material removal, along a line of a specified form, preferably a straight line. Preferably, for ascertaining the feature there can be carried out a Hough transformation or a Fast-Hough transformation or a modification of one of these transformations for the deviation data of the deviation data record which correspond to places for which the deviation data of the deviation data record indicate an irregularity of the at least one specified type, for example an irregularity in the form of an adhesion and/or crease or to an irregularity in the form of a material removal. This alternative allows a particularly clear recognition of adhesive strips which mostly are affixed straight.

A still further preferred alternative provides that for deviation data indicating an irregularity of the at least one specified type, for example an irregularity in the form of an adhesion and/or a crease or a material removal, a blob analysis is carried out and a property of the ascertained blobs or areas corresponding to these, preferably the number of places therein, particularly preferably only the number of places in the largest blob or area corresponding thereto, is employed as a feature. A blob designates here a set of places which form a coherent area and whose deviation data indicate an irregularity of the at least one specified type, for example an irregularity in the form of an adhesion and/or crease or an irregularity in the form of a material removal.

In a particularly preferably development, as a feature there can be ascertained a measure for the places in the ascertained sets respectively lying within a form enclosing the places as close as possible. For example, the ratio from the number of places and the area given by the form may be employed.

Upon checking whether an indication of an irregularity of the at least one specified type, for example an irregularity in the form of at least one adhesion, preferably an adhesive strip, and/or a crease and/or on an irregularity in the form of a material removal is present on the value document, there may preferably be carried out a classification by means of a support vector machine using the at least one feature or the features. This has the advantage, that a more accurate classification is made possible.

It is then particularly preferred that upon checking there is ascertained a probability that for the specified ultrasound data record there was ascertained an irregularity of the at least one specified type, for example an irregularity in the form of an adhesion, preferably an adhesive strip, or a crease or a material removal. For ascertaining this probability there may be employed parameters which are ascertainable using ultrasound training data records which were captured for training value documents of the specified value document having irregularities of the at least one specified type, for example an irregularity in the form of at least one adhesion, preferably an adhesive strip, or at least one crease or with irregularities in the form of at least one material removal, and for training value documents of the specified value document type without irregularities of the at least one specified type, preferably depending on the at least one specified type, irregularities in the form of at least one adhesion, preferably an adhesive strip, or at least one crease or at least one material removal.

The embodiments discussed hereinbefore do not only apply to the method, even if they are described only in connection with the method, but accordingly also for the apparatus or the computer program.

Subject matter of the invention is further an apparatus for processing value documents with a feeding device for feeding value documents, an output device for receiving processed, i.e. sorted value documents, and a transport device for transporting singled value documents from the feeding device to the output device. The apparatus further comprises an apparatus according to the invention for checking the transported value documents.

For ascertaining the parameter employed upon checking there is mostly required a large number of ultrasound training data records for value documents of the specified type having an irregularity of the at least one specified type, preferably an irregularity in the form of an adhesion and/or a crease or a material removal. However, those are not always available and may have to be prepared.

The subject matter of the invention is hence also a method for generating ultrasound training data for adapting parameters of a method for checking a value document of a specified value document type for the presence of at least one irregularity of at least one specified type, preferably an irregularity in the form of at least one adhesion, preferably an adhesive strip, and/or at least one crease and/or at least one irregularity in the form of at least one material removal, in which for specified reference value documents of the specified value document type there are captured ultrasound data records which respectively describe in locally resolved fashion at least one ultrasound property, preferably the ultrasound transmission, of the respective reference value document, the specified reference value documents not having an irregularity of the at least one specified type, preferably, depending on the at least one specified type, an irregularity in the form of at least one adhesion, preferably an adhesive strip, and/or at least one crease and/or an irregularity in the form of at least one material removal. At least some of the ultrasound data records are stored as ultrasound training data records. Furthermore, from at least some of the ultrasound data records, which may or may not be included at least partially in the already stored ultrasound training data records, there are generated further ultrasound training data records, by changing the ultrasound data of the ultrasound data record for respectively given places in such a way that the change corresponds to a given irregularity of the specified type, for example given adhesion or crease or a given material removal. These further ultrasound training data records are also stored. Preferably, the parameters of the checking method are adapted using the ultrasound training data records.

For the capture of the ultrasound data records, the explanations regarding the checking method apply accordingly here. This procedure has the great advantage that a very large number of ultrasound training data records can be easily produced without great effort. The change can be easily executed by means of a data processing device.

It is preferred here that upon the generation of one of the further ultrasound training data records the places are respectively given such that the form and/or the position of the irregularity of the specified type, for example the adhesion or crease or the material removal, is chosen from a specified set of possible forms or positions. In particular, the positions and, where applicable, also the forms may be randomly chosen within the specified region.

Furthermore, it is preferred, that upon the generation of one of the further ultrasound training data records or of one of the further ultrasound training data records, the quantity of the change by the irregularity of the specified type, for example, by the given adhesion or crease or the given material removal, is chosen from a specified region or a specified set. The set of the changes may comprise, for example, the changes by adhesive strips of different specified thicknesses.

The explanations regarding the checking method apply accordingly to the types of irregularity.

BRIEF DESCRIPTION OF THE DRAWINGS

The invention will hereinafter be explained further by way of example with reference to the drawings, in which FIG. 2 shows a schematic representation of a transmission ultrasound sensor of the apparatus in FIG. 1, FIG. 3 shows a schematic representation of an arrangement of ultrasonic transducers of the transmission ultrasound sensor in FIG. 2, which serve as ultrasound transmitters, in a plane parallel with a transport direction of the value documents, FIG. 4 shows a schematic representation of a value document with watermark, security thread and an adhesion in the form of an adhesive strip.

DETAILED DESCRIPTION OF VARIOUS EMBODIMENTS

Figure 1:
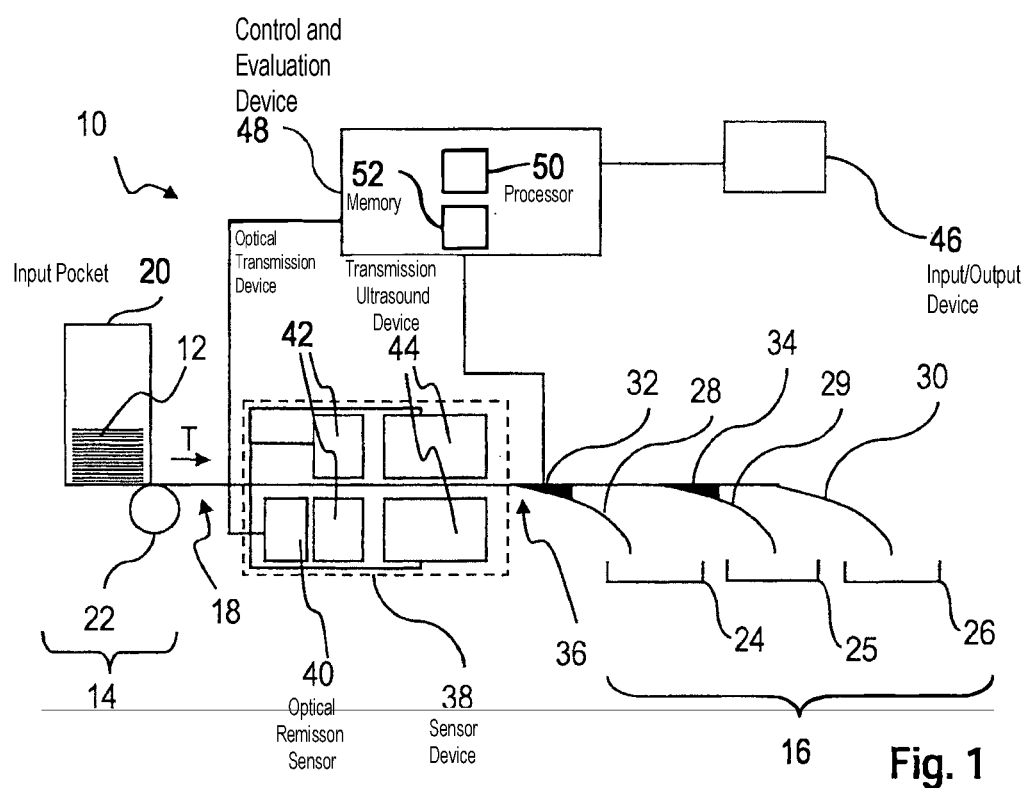
FIG. 1 shows a schematic view of a value-document processing apparatus in the form of a bank-note sorting apparatus.

A value-document processing apparatus 10 in FIG. 1, in the example an apparatus for processing value documents 12 in the form of bank notes, is configured for sorting value documents in dependence on the recognition of the authenticity and of the state of processed value documents. The components of the apparatus described in the following are arranged in a housing (not shown) of the apparatus or are held at this, unless they are referred to as external.

The apparatus has a feeding device 14 for feeding value documents, an output device 16 for receiving processed, i.e. sorted value documents, and a transport device 18 for transporting singled value documents from the feeding device 14 to the output device 16.

The feeding device 14 comprises, in the example, an input pocket 20 for a value-document stack and a singler 22 for singling value documents from the value-document stack in the input pocket 20 and for feeding the singled value documents to the transport device 18.

The output device 16 has, in the example, three output portions 24, 25 and 26 into which processed value documents can be sorted, sorted according to the result of the processing. In the example, each of the portions has a stack pocket and a stacking wheel (not shown) by means of which fed value documents can be deposited in the stack pocket.

The transport device 18 has at least two, in the example three, branches 28, 29 and 30 at whose ends one of the output portions 24 or 25 or 26 is disposed respectively, and, at the branching points, gates 32 and 34 controllable by actuating signals for feeding value documents to the branches 28 to 30 and thus to the output portions 24 to 26 in dependence on actuating signals.

On a transport path 36, defined by the transport device 18, between the feeding device 14, in the example more precisely the singler 22, and the first gate 32 after the singler 22 in the transport direction there is disposed a sensor device 38 which measures physical properties of the value documents when value documents are being transported past, and forms sensor signals representing the measurement results. In this example, the sensor device 38 has three sensors, namely an optical remission sensor 40 which captures a remission color image and a remission IR image of the value document, an optical transmission sensor 42 which captures a transmission color image and a transmission IR image of the value document, and a transmission ultrasound sensor 44 which captures or measures the ultrasound transmission of the value document in locally resolved fashion as an ultrasound property and will hereinafter only be referred to as an ultrasound sensor for simplicity's sake. The sensor signals formed by the sensors correspond to measurement data or raw data of the sensors, which, depending on the sensor, could already have been subjected to a correction, for example in dependence on calibrating data and/or noise properties.

For capturing and displaying operating data, the value-document processing apparatus 10 has an input/output device 46. The input/output device 46 is implemented, in the example, by a touch-sensitive display device ("touch screen"). In other embodiment examples, it may comprise, for example, a keyboard and a display device, for example an LCD display.

A control and evaluation device 48 is connected via signal connections to the sensor device 38, the input/output device 46 and the transport device 18, in particular the gates 32 and 34.

The control and evaluation device 48 forms a data processing device and has, besides corresponding data interfaces (not shown in the Figures) for the sensor device 38 or their sensors, a processor 50 and a memory 52 connected to the processor 50, in which at least one computer program with program code is stored, upon the execution of which the control and evaluation device 48 or the processor 50 controls the apparatus according to the properties of the value documents. Thus, in its function as an evaluation device it may evaluate the sensor signals, in particular for ascertaining an authenticity class and/or a state class of a processed value document, and in its function as a control device it may drive the transport device 18 in accordance with the evaluation and optionally store the measurement data. In other embodiment examples there may also be provided an evaluation device separate from the control device, which is connected via interfaces to the sensors of the sensor device 38, on the one hand, and the control device, on the other hand. The evaluation device is then configured for analysing the sensor signals and delivers the respective result to the control device which drives the transport device. The evaluation operations described in the following may then be carried out by the evaluation device alone.

Further, the control and evaluation device 48 drives the input/output device 46 such, among other things, that it displays operating data, and captures via these operating data which correspond to inputs of an operator.

In operation, value documents are singled from the feeding device and transported past or through the sensor device 38. The sensor device 38 captures or measures physical properties of the value document respectively transported past or through it and forms sensor signals or measurement data which describe the measurement values for the physical properties. The control and evaluation device 48 classifies the value document in dependence on the sensor signals of the sensor device 38 for a value document and on classification parameters stored in the evaluation device into one of specified authenticity and/or state classes, and by emitting actuating signals drives the transport device 18, here more precisely the gates 32 or 34, such that the value document is output, corresponding to its class ascertained upon the classification, into an output portion of the output device 16 which is associated with the class. The association with one of the specified authenticity classes or the classification is effected here in dependence on at least one specified authenticity criterion.

Aspects of the formation and employment of ultrasound measurement data are described in more detail in the following.

For the locally resolved capture of the ultrasound property, in the example the ultrasound transmission, there serves the transmission ultrasound sensor 44 which is constructed in the example as follows (cf. FIGS. 2 and 3).

The ultrasound sensor 44 has several ultrasound transducers 54 arranged transverse to a transport direction T of the value documents 12 as well as in parallel with this substantially in a plane in parallel with one along the transport path 36 of the transported value document 12, driven by the control and evaluation device 48 for emitting ultrasound pulses onto the value document. These ultrasound transducers 54 thus serve as ultrasound transmitters.

Opposite, relative to the transport path 36, to the ultrasound transducers or transmitters 54, the same number of ultrasound transducers 56 serving as ultrasound receivers is arranged in such a way that these may receive ultrasound waves emitted by a value document 12 transported along the transport path 36 and caused by acoustic irradiation with ultrasound pulses of the ultrasound transmitters 54. The ultrasound transducers 56 are connected with the control and evaluation device 48 via interfaces (not shown in the Figures) and schematically shown signal connections.

Each of the ultrasound transmitters 54 has associated therewith one of the ultrasound receivers 56 such that there arises between these an ultrasound path 58 extending at least approximatively orthogonal to a value document 12 transported along the transport path 36, along which path an ultrasound pulse emitted by the respective ultrasound transmitter 54 runs to the ultrasound receiver 56 associated therewith. With every pair of ultrasound transmitters and ultrasound receivers associated therewith or with every ultrasound path 58 in connection with the control and evaluation device 48, a value for the ultrasound transmission of the value document 12 at the place acoustically irradiated with ultrasound is thus ascertainable.

The ultrasound transducers 54 or 56 are configured such that they are well suited for emitting or for receiving ultrasound pulses, respectively, with a duration in the region of about 30 µs in the example and an ultrasound frequency, i.e. a frequency maximum of the spectrum of the ultrasound pulse, of about 400 kHz in the example. Further, they are dimensioned such that respectively one dot, i.e. scan region, on a value document 12 transported along the transport path 36, which dot is acoustically irradiated with the ultrasound pulses upon acoustic irradiation, has a diameter of about 2 mm. Each of the scan regions has associated therewith the center of the scan region as a place.

The ultrasound transmitters 54 and the ultrasound transducers 56 respectively associated therewith, in the example are arranged offset in two lines extending transverse to the transport direction. The ultrasound transducers of a respective line are arranged in the same distances to each other and are operated simultaneously. The ultrasound transducers, however, are arranged in the lines such that the ultrasound transducers of the one of the lines transverse to the transport direction are arranged offset opposite the ultrasound transducers of the other one of the lines.

The ultrasound transducers of all the lines are operated in synchronously pulsed fashion. When a value document 12 is transported with a constant, suitably specified speed through the ultrasound paths 58, ultrasound transmission values are thus captured in specified time intervals during the transport. In this embodiment example, the driving is effected independent of a value document 12 entering the capture region of the transmission ultrasound sensor 44. For suppressing an undesirable reception of ultrasound pulse echoes, the respective ultrasound receiver for an ultrasound path may be switched on with a delay, relative to the time of the ultrasound transmitter emitting the ultrasound pulse for the ultrasound path, by somewhat less than the pulse runtime for the ultrasound path and switched off before the double pulse runtime since the emitting.

By offsetting the ultrasound transducers of the lines to each other and their alternate operation there arises a regular arrangement of scan regions or places on the value document 12, in the example an arrangement on a rectangle grid which is schematically shown by way of example in FIG. 4. The arrangement of the ultrasound transmitters and ultrasound receivers 54 or 56 is chosen such that the distance of consecutive places in transport direction T is smaller than 1 cm, preferably smaller than 5 mm. In the example, the distance of most adjacent places is about 3 mm, preferably 2 mm.

The ultrasound sensor 44 in the embodiment example has in particular more than twenty-four pairs of ultrasound transmitters/receivers or ultrasound paths 58, which are arranged such that the corresponding places have a distance between 3 and 4 mm.

For capturing the transmission values, i.e. the transmission, the control and evaluation device 48 captures the sensor signals of the ultrasound receivers 56 in constant time intervals, which reproduce the intensity or power of individual received ultrasound pulses as a function of time and thus, because of the constant transport speed, also of place. On the basis of these signals the control and evaluation device 48 also ascertains the entry of the value document into the capture region of the transmission ultrasound sensor 44. The transmission values are here simply given, assuming a basically constant transmitting power of the ultrasound transmitters 54, by the received ultrasound pulse energies. In other embodiment examples, however, it is also possible to divide the received ultrasound pulse energies by a specified or measured ultrasound pulse energy of transmitted pulses and to thus obtain normalized transmission values.

The ascertained ultrasound transmission values are stored associated with the places for which they were captured and form an ultrasound data record for the value document. The storage can be effected, for example, in such a way that respectively upon operation of the ultrasound transducers of one of the lines the ultrasound transmission values for the ultrasound transducers of the respective line are successively stored in a specified order, whereby corresponding to the alternate operation of the ultrasound transducers of the lines the ultrasound transmission values of ultrasound transducers of the respectively operated line are stored in the memory 50 after the ultrasound transmission values of ultrasound transducers of the line operated respectively before that. In particular, the ultrasound transmission values can be stored as a vector whose index indicates the place for which a respective ultrasound transmission value was captured. The index indicating the position in the vector then represents, together with the instruction for the conversion of places or place coordinates into index values, the place information. In the present embodiment example, ultrasound transmission values for N places on the respective value document are captured for value documents of the specified value document type.

The frequency with which the ultrasound pulses are successively emitted and the transport speed of the value document are chosen such that along the transport direction of the value document there are captured ultrasound transmission values in a distance of 3 mm, preferably 2 mm, along the transport direction or fifty or more transmission values.

In the present embodiment example of a method for checking value documents of a specified value document type for the presence of at least one irregularity in the form of at least one adhesion or a crease, the ultrasound transmission values are employed to check a respective value document for whether it has an irregularity in the form of an adhesion or a crease. There is thus effected a check for the presence of an irregularity of at least one specified type, the specified types being adhesions and creases. If such an adhesion or crease is recognized, the value document is associated with the state class "unfit for circulation". The adhesion here is an oblong adhesive strip which is affixed at least on one side to the value document and adheres thereto. This is illustrated in FIG. 4, which shows a value document 60 of a specified value document type with a watermark 62 represented in dots, a security thread 64 and an adhesive strip 66 marked by hatching.

The watermark 62, the security thread 64 and the adhesive strip 66, but also a crease lead to changes in the ultrasound transmission in comparison to the other regions of the value document which are formed from a substrate of substantially constant thickness and density. In particular, adhesive strips reduce the ultrasound transmission. The watermark, however, increases the ultrasound transmission on account of the partially reduced weight per unit area. The exact position and configuration of the watermark 62 and the exact position of the security thread 64 on the respective value document are not exactly constant for value documents of the specified value document type, but my vary substantially within specified regions for different value documents of the specified type. This may impede the recognition of adhesive strips.

In the method there is employed a model for the location dependence of the ultrasound transmission of the value documents of the specified value document without adhesions, creases or damages, for example tears or holes. The model defines model data records which lie within a specified partial region of an N-dimensional space of possible ultrasound data. N is here the number of the places for which the ultrasound property was captured and hence the number of the measurement results of the ultrasound data record. This model may be ascertained as follows:

First, reference value documents of the specified value document type without adhesions, creases or damages are specified. Preferably, the number of reference value documents is higher than 100.

For these reference value documents 44 there are captured, by means of the transmission ultrasound sensor, reference ultrasound data records which describe in locally resolved fashion the ultrasound transmission of the reference value documents for ultrasound of the ultrasound sensor 44.

For this purpose, the ultrasound data records may be regarded as vectors whose index reproduces the place at which the ultrasound transmission value corresponding to the index was captured.

For fixing the partial region, the model data records may be represented by a sum of a mean vector and a linear combination of partial-region vectors. A mean vector and unit vectors $e_j$ orthogonal to each other with N components or of the dimension N are now ascertained, which describe the reference ultrasound data records as well as possible. The number K of the unit vectors is smaller than N and is chosen in dependence on the available computing capacity and the still acceptable error as well as the number of the available reference ultrasound data records. The index j assumes integer values from 1 to K. The reference value documents, for the following representation, are designated with an index i running from 1 to the number M of the reference value documents.

In the following, $x_i$ designates the N-dimensional vector representing the reference ultrasound data record for the reference value document i; as a mean vector the mean value of $x_i$ over the reference value documents is employed and designated as an N-dimensional vector m:

$$m = \frac{1}{M} \sum_i x_i$$

An approximation $y_i$ for a reference ultrasound data record $x_i$, again representable as an N-dimensional vector, is then represented as a sum of the mean vector or a mean value m and a linear combination of the unit vectors $e_j$ with scalar coefficients $a_{ij}$:

$$y_i = m + \sum_{j=1}^{K} a_{ij} e_j$$

By a suitable choice of the coefficients $a_{ij}$ and of $e_j$, the error E between the approximations and the reference ultrasound data records $$E = \sum_{i=1}^{M} \| y_i - x_i \|^2$$

is to be minimized, for which purpose known optimization methods with Lagrange multipliers may be employed.

The solution for the choice of the unit vectors $e_j$ is given by the K normalized eigenvectors $v_j$ for the greatest eigenvalues of the scattering or covariance matrix $\Sigma$ $$\Sigma = \frac{1}{M-1} \sum_{i=1}^{M} (x_i - m)(x_i - m)^T$$

The superscript T designates here the transposed vector or further below in connection with matrices the transposed matrix, $x_i$ and m are column vectors. The factor $1/(M-1)$ is irrelevant in the following and can then be omitted.

K is chosen here preferably such that the error E is smaller than a specified value.

The model obtained in this way hence defines model ultrasound data records z which are defined by the sum of the mean value vector m and a linear combination of the normalized eigenvectors $v_j$:

$$z = m + \sum_{j=1}^{K} s_j v_j$$

$s_j$ being scalar coefficients. The vectors z are vectors in the N-dimensional space.

This model is hence a model for the location dependence of the ultrasound transmission of reference value documents of the specified value document type without irregularities in the form of adhesive strips or creases.

For a captured ultrasound data record represented by the vector x, the best approximation can be determined through the model or the minimal deviation from the model, by minimizing, through adapting the coefficients $s_j$, the errors between the vector x and the model data records given by the set of possible vectors z. The specified deviation measure for the deviation between the ultrasound data record and a model data record is given by the norm of the difference between the ultrasound data record and the model data record, the norm of a vector being the root of the sum of the squares of the vector components.

If B designates the matrix $(v_1 \ldots, v_k)$, the K-dimensional vector will be $\hat{s}' = (\hat{s}_1 \ldots, \hat{s}_k)^T$ of the coefficients of the linear combination $$\hat{s} = B^T(x-m), \quad (1)$$

i.e. the model data record with the minimal deviation from the ultrasound data record x is given by $$z = m + \sum_{j=1}^{K} \hat{s}_j v_j. \quad (2)$$

The deviation data record is given by the deviation vector $$R = x - (m + B\hat{s}) = x - [m + BB^T(x-m)] \quad (3)$$

For the calculation of the deviation data record there are hence only required the components of the mean value vector m and that of the matrix $B \cdot B^T$ which must be ascertained and stored for a given value document type.

For checking whether an indication of an irregularity in the form of at least one adhesion, in particular an adhesive strip, or at least one crease is present on the value document, features are ascertained in dependence on the deviation data record.

The following features are employed in this embodiment example:

The first feature $M^{(1)}$ relates to or describes the quantity of the deviation described by the deviation data record. More precisely, this embodiment example is given the feature by the Euclidean or L2 norm of the vector representing the deviation data record $$M^{(1)} = \|R\|_2.$$

The second feature $M^{(2)}$ represents a measure for the magnitude of the deviations at places at which a difference between ultrasound transmission and model ascertainable from the deviation data of the deviation data record indicates an irregularity in the form of an adhesion or crease. As an adhesion or crease reduces the ultrasound transmission, for a place with an adhesion or crease the deviation or the deviation datum of the deviation data record is smaller than zero. The feature is given by $$M^{(2)} = \sum_{n=1}^{N} R_n \Theta(-R_n),$$

$\Theta(t)$ being the Heaviside function, i.e. $\Theta(t)=0$ for $t<0$, 1 for the others.

The third feature $M^{(3)}$ represents a measure for places, for which the deviation data of the deviation data record indicate an irregularity in the form of an adhesion or crease, occurring spatially cumulated, the measure also taking into account the quantities of the deviations. An energy function is employed here, which comprises a sum of contributions which respectively include products of deviation data at different places, weighted with a weighting factor depending on the distance of the places; here, preferably only deviation data are taken into account which indicate an irregularity in the form of at least one adhesion, preferably an adhesive strip, or at least one crease. More precisely, the Ising energy is employed for places with a reduced ultrasound transmission with an interaction with the next eight neighbors:

$$M^{(3)} = \sum_{n,m=1, n \neq m}^{N} w_{nm} \theta(-R_n) \theta(-R_m) R_n R_m,$$

wherein $w_{nm}=1$ when the places corresponding to n and m are nearest neighbors, $w_{nm}=1/\sqrt{2}$, when the places corresponding to n and m are next but one or next nearest neighbors, and $w_{nm}=0$ for the others.

The fourth feature $M^{(4)}$ represents a measure for the presence of deviations which indicate an irregularity in the form of at least one adhesion or crease, along a line of a specified form, in the example a straight line. In this embodiment example, for this purpose, a Hough transformation is carried out for those places whose deviation data of the deviation data record indicate an irregularity in the form of an adhesion or crease, hence are negative here. In the Hough transformation for the recognition of straight lines, parameter pairs which define a straight line in the space of the places are ascertained for possible straight lines between two of the examined places in each case. The region of possible value pairs for the parameter pairs is divided into cells of a specified size, which respectively have associated therewith a counter. If a parameter pair falls in one of the cells, the value thereof is incremented by one. As a feature there is now employed the maximum counter value, ascertained from all the cells, normalized with the number of the places employed upon the transformation.

Upon checking whether an indication of an irregularity in the form of at least one adhesion, in particular an adhesive strip, or a crease is present on the value document, a classification based on the features is carried out by means of a support vector machine with non-linear core or kernel function. For training there are employed training value documents of the specified value document type in a specified orientation, which have no irregularities have in the form of at least one adhesion, in particular an adhesive strip, or a crease, and those which have this one of one of these irregularities. The number of training value documents be L.

In the following, C or $C_1$ shall designate a vector formed of the feature values of the mentioned features for a captured ultrasound data record x or a reference ultrasound data record $x_l$, whereby the index 1 may run from 1 to L. For this purpose, a distance function f is employed, which is given by $$f(C) = \sum_{l=1}^{L} \alpha_l k(C, C_l) + b.$$

The decision function, which may assume the values +1 and −1, is then given by $$c(C) = \text{sign}(f(C)).$$

The sign(t) is here a function, which is 1 if t≥0 and −1 for the others. The coefficients $\alpha_l$ and the constant b may be ascertained by solving a square optimization problem.

In the present example, a core or kernel function k with radial base functions is employed:

$$k(C, C_l) = \exp(-\|C - C_l\|^2 / (2\sigma^2)).$$

The parameter σ is to be chosen suitably here, where applicable by trying.

The result of the classification is binary, i.e. it is only ascertained whether or not an indication of an irregularity in the form of an adhesive strip or a crease is present (f(C)=1) or not (f(C)=−1).

The above-mentioned values and parameters are stored in the memory 52 for each value document type which can be checked by means of the apparatus 10.

Figure 5:
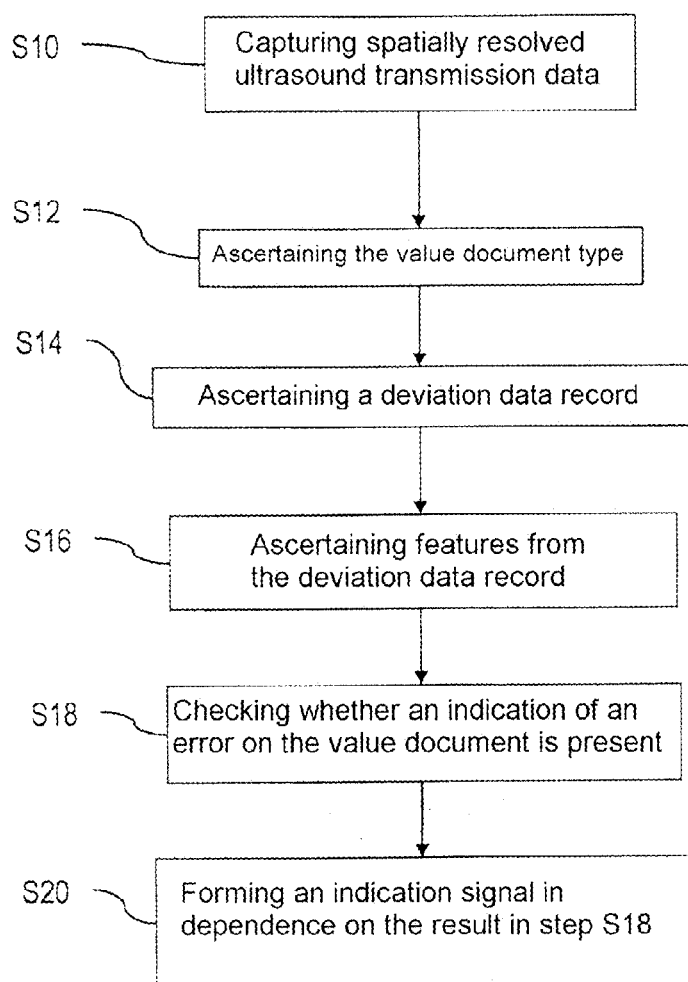
FIG. 5 shows a simplified flowchart of a first embodiment of a method for checking value documents for the presence of an irregularity in the form of an adhesion or crease, which can be carried out by means of the apparatus in FIG. 1.

FIG. 5 shows a first embodiment example of a method for checking a value document of a specified value document type for the presence of at least one irregularity in the form of at least one adhesion, here an adhesive strip, or a crease. For carrying out the method, in the control and evaluation device 48, more precisely the memory 52 thereof, there is stored a computer program upon the execution of which the control and evaluation device 48, more precisely the processor 50, executes the first embodiment of the method.

In step S10 an ultrasound data record which describes in locally resolved fashion an ultrasound property, in this example the ultrasound transmission, of the value document is captured by means of the transmission ultrasound sensor 44 for a value document. The transmission ultrasound sensor 44 captures, as described hereinbefore, the ultrasound transmission for measuring dots on the value document and forms respective measurement values which are associated with the ultrasound data record. The ultrasound data record corresponds to the vector x. The measurement values or the ultrasound data record are captured by the control and evaluation device 48.

Then the evaluation device 48 ascertains in step S12 on the basis of an image of the value document captured by means of the optical remission sensor 40 the value document type and orientation thereof.

In step S14 the evaluation device 48 ascertains the deviation data record which is represented above by the vector R. This vector describes in locally resolved fashion a deviation between the ultrasound data record and the model data record and is ascertained such that the deviation described thereby is minimal with respect to the model. For this purpose, only the right side of the equation (3) has to be calculated.

In step S16 the evaluation device 48 ascertains, for carrying out the check whether an indication of an irregularity in the form of at least one adhesion, in particular an adhesive strip, or a crease is present on the value document, the features $M^{(1)}$ to $M^{(4)}$.

The evaluation device 48 employs the calculated features in step S18 to check whether an indication of an irregularity in the form of at least one adhesion, in particular an adhesive strip, or a crease is present on the value document. For this purpose, it employs the above-described support vector machine. The result in this embodiment example is binary, i.e. the result is +1, if the classification yields a presence of an adhesive strip or a crease, otherwise 0. The evaluation device 48 stores a corresponding value.

In step S20 it then forms in dependence on the result of step S18 an indication signal indicating whether or not the check has yielded the presence of an irregularity in the form of an adhesion, in this case an adhesive strip, or a crease.

The result or the indication signal is employed by the control and evaluation device 48 for ascertaining a sorting result in dependence on the results of other checks, and to drive the transport device 18, more precisely their gates, so that the value document is transported into an output portion associated with the sorting result.

Figure 6:
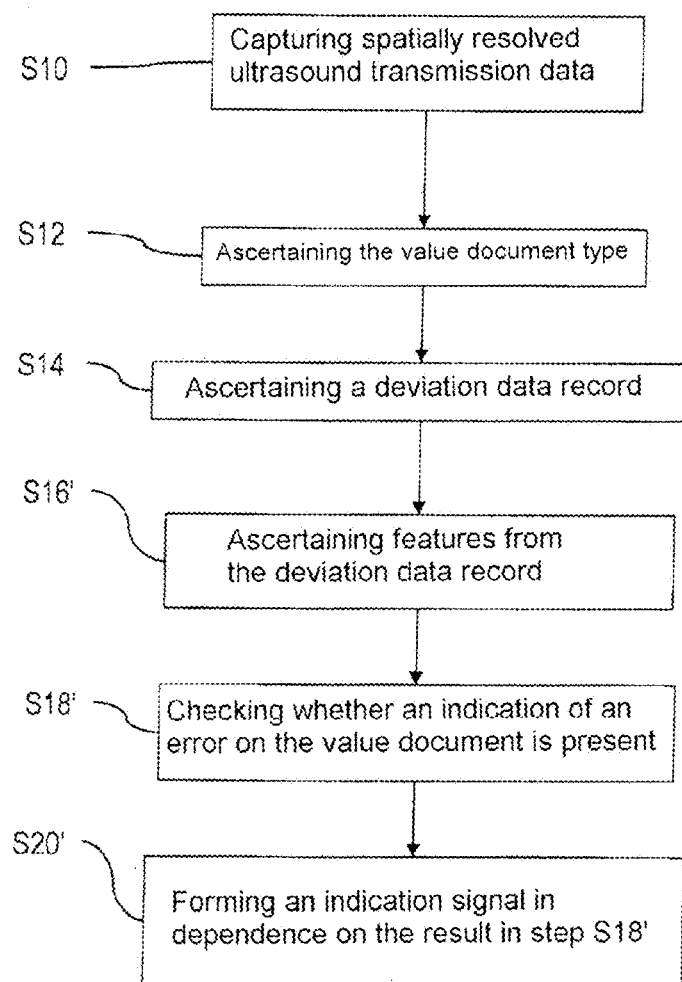
FIG. 6 shows a simplified flowchart of a second embodiment of a method for checking value documents for the presence of an irregularity in the form of an adhesion or crease, which can be carried out by means of the apparatus in FIG. 1.

A second embodiment example in FIG. 6 differs from the first embodiment example in FIG. 5 only in that the steps S16 to S20 are replaced by steps S16' to S20'. Accordingly, the control and evaluation device and the computer program stored therein are amended.

The step S16' differs from step S16 in that the second feature $M^{(2)}$ is replaced by a feature $M^{(6)}$, on the one hand. The latter likewise describes a measure for the magnitude of the deviations at places at which a difference between ultrasound transmission and model ascertainable from the deviation data of the deviation data record indicates an irregularity in the form of an adhesion or crease. The feature is given by $$M^{(6)} = \sum_{n=1}^{N} R_n^2 \Theta(-R_n)$$

On the other hand, step S16' differs from step S16 in that a further feature $M^{(7)}$ is employed which describes a probability that the model data record, which corresponds to the deviation data record, occurs according to the model. The model data record corresponding to the deviation data record is that model data record for which the deviation from the model is minimal.

For this purpose, in this embodiment example it is assumed that the ultrasound data records are normally distributed in well enough approximation. As a parameter of the distribution the mean value and the covariance matrix are ascertained. This is effected analogously to the first embodiment example, whereby as the mean value there is ascertained the mean vector and as the covariance matrix the above-mentioned covariance matrix $\Sigma$. By a main component analysis of the distribution one reaches the model described above, which is supplemented by the statement of a probability that a value document of the specified value document type without an irregularity in the form of an adhesion, in the example an adhesive strip, or crease has a model ultrasound data record according to the equations (1) and (2) as the best approximation. The logarithm of the probability for the occurrence of a model data record is then given by $$z = m + \sum_{j=1}^{K} s_j v_j$$

$$\log(p(s \mid \text{error} - \text{free})) = \log\left[(2\pi)^{-\frac{K}{2}} \mid \Sigma_s \mid^{-\frac{1}{2}} \exp\left(-\frac{1}{2} s^T \Sigma_s^{-1} s\right)\right]$$

with the diagonal matrix $$\Sigma_s = \begin{pmatrix} \lambda_1 & \cdots & 0 \\ \vdots & \ddots & \vdots \\ 0 & \cdots & \lambda_K \end{pmatrix}$$

of the K greatest eigen-values of the covariance matrix $\Sigma$. As a feature $M^{(7)}$ then the logarithm of the probability that the model data record occurs with the minimal deviation from the ultrasound data record according to the equations (1) and (2)

$$M^{(7)} = \log(p(\hat{s} \mid \text{error} - \text{free})) = \log\left[(2\pi)^{-\frac{K}{2}} \mid \Sigma_s \mid^{-\frac{1}{2}} \exp\left(-\frac{1}{2} \hat{s}^T \Sigma_s^{-1} \hat{s}\right)\right]$$

is employed.

Already because of the different features, step S18 is replaced by step S18'. The support vector machine and their parameters are replaced using the reference ultrasound data records analogous to the support vector machine of the first embodiment example.

Accordingly, an indication signal which represents the value obtained in step S18' is formed in step S20'.

Figure 7:
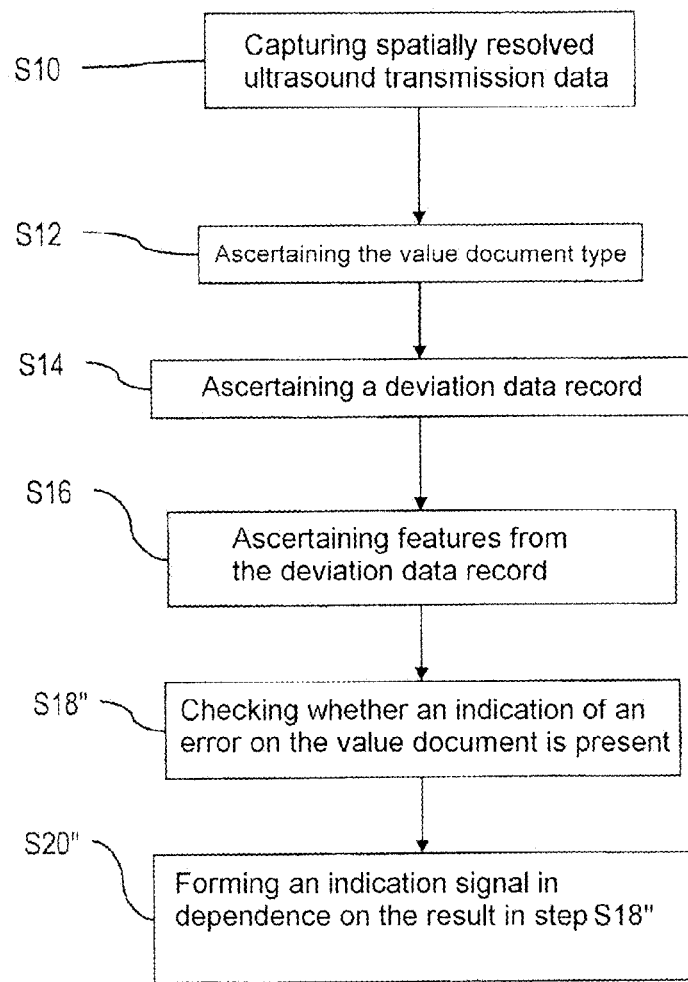
FIG. 7 shows a simplified flowchart of a third embodiment of a method for checking value documents for the presence of an irregularity in the form of an adhesion or crease, which can be carried out by means of the apparatus in FIG. 1.

A third embodiment example illustrated in FIG. 7 differs from the first embodiment example in that the step S18 and accordingly the step S20 are replaced by the steps S18" and S20". More precisely, in step S18 the accordingly modified control and evaluation device 48 does not ascertain a classification result in the form of one of two classes as a result; upon checking it ascertains as a result a probability that for the specified ultrasound data record an irregularity in the form of an adhesion, preferably an adhesive strip, or a crease was ascertained.

This is a probability that a class, which upon the classification was obtained using the support vector machine, is appropriate for the given ultrasound data record, in particular for example that an adhesive strip or a crease is present when the ultrasound data record is given. This value is stored, as in the first embodiment example.

For this, in the present embodiment example there is employed the following relation (cf. Platt, John C., "Probabilistic Outputs for Support Vector Machines and Comparisons to Regularized Likelihood Methods", Advances in Large Margin Classifiers, 1999, pages 61 to 74):

$$p(c = 1 \mid x) = \frac{1}{1 + \exp(Af(x) + B)}.$$

The parameters A and B required therefor may be ascertained like the parameters for the support vector machine and be stored in the memory 52.

A fourth embodiment example differs from the first embodiment example in that the possible model data records are given by the mean value. The formulae to be employed then result from the fact that the unit vectors are omitted.

The fifth embodiment example differs from the above-described embodiment examples in that instead of the feature $M^{(3)}$ there is employed a feature $M^{(8)}$ which also relates to a measure for places, for which the deviation data of the deviation data record indicate an irregularity in the form of an adhesion or a crease, occurring spatially cumulated. For this purpose, the control and evaluation device carries out, after ascertaining the deviation data which indicate an irregularity in the form of an adhesion or crease and hence are negative here, a blob analysis for these ascertained deviation data. A blob designates here a set of places which form a coherent area and whose deviation data indicate an irregularity in the form of an adhesion or crease.

As a feature $M^{(8)}$ there is then employed the number of places in the greatest ascertained set.

In developments of this embodiment example, as a further feature there can be ascertained a measure for the places in the ascertained sets or blobs respectively lying within a form enclosing the places as close as possible, in the example a parallelogram. For this, the relation of the number of places of the respective blob and the area of the parallelogram or rectangle may be employed as a feature.

Yet a further embodiment example differs from the above-described embodiment examples in that before the ascertainment of the deviation data record it is checked by the control and evaluation device whether ultrasound data of the ultrasound data record correspond to problem regions of the value document, for example to holes, tears or dog-ears. In the case of dog ears, the problem region comprises, on the one hand, the portion from which the corner of the value document corresponding to the dog-ear was folded out, and on the other hand, the portion over which the corner was laid by folding.

For this, there may be employed an image of the optical remission sensor or preferably of the optical transmission sensor. Alternatively, the ultrasound transmission data may be compared with a specified threshold value. If a respective ultrasound transmission value exceeds the threshold value for a place, this corresponds to a problem region or lies within this region.

If a place corresponds to a problem region or if a place lies within a problem region, the ultrasound transmission value is replaced by a replacement transmission value specified for the place, which is characteristic for an intact value document of the specified value document type. In the example, as a replacement transmission value there is employed the ultrasound transmission value of the mean vector at the same place. The other method steps are unchanged.

The described steps and features of the described embodiment examples may be exchanged or combined.

For ascertaining the ultrasound training data records, the following method may be executed for generating ultrasound training data for the adaptation of parameters of a method for checking a value document of a specified value document type for the presence of at least one irregularity in the form of at least one adhesion, in the example an adhesive strip, or at least one crease. In the following the ultrasound training data or ultrasound training data records are referred to only as training data or training data records, for simplicity's sake.

For the specified reference value documents which were employed for ascertaining the model, ultrasound data records are captured which respectively describe in locally resolved fashion at least one ultrasound property, preferably the ultrasound transmission, of the respective reference value document. These are captured preferably with the same ultrasound transmission sensor. These reference value documents do not have, as they were also employed for the adaptation of the model, an irregularity in the form of at least one adhesion or, here, an adhesive strip or a crease. These ultrasound data records are stored as training data records. For each of these training data records further training data records are now generated by means of a data processing device, which correspond to value documents of the specified value document type having at least one irregularity in the form of an adhering adhesive strip or a crease.

The places for changes are given such that the form and/or position of the adhering adhesive strip or of the crease are chosen from a specified set of possible forms or positions. Further, the quantities of the changes of the ultrasound transmission by the adhesive strip or the crease are chosen from a specified region. For this, regions for the possible lengths, widths and thicknesses of adhesive strips are specified. Further, it is assumed that the adhesive strips may be randomly inclined relative to the edges of the respective value document and offset relative to the edges. Further, the adhesive strips be of a rectangular form, as long as they do not reach beyond the edge of the value document. In the latter case it is assumed that the adhesive strips end on the edge of the value document.

Now, the orientation, i.e. position and inclination on the value document, and the form, length and width, among other things, as well as the thickness of the adhesive strip or the orientation and form of a crease are randomly chosen within the respectively given region. For the places given by the position and the form, the ultrasound data of the ultrasound data record for the reference value document are then changed such that the change of the ultrasound transmission corresponds to a sound intensity reduction or sound amplitude reduction by an adhesive strip of the given thickness or a crease. The further training data records generated in this way are stored.

These training data records can then be employed instead of the training data mentioned in the previous embodiment examples or in addition to these.

Further embodiment examples differ from the above-described embodiment examples in that instead of the check for an irregularity in the form of at least one adhesion or crease there is carried out a check for irregularities in the form of material removals on value documents having a polymer layer which has an opaque cover applied thereon. The feature $M^{(4)}$ is then not used. Further, the formulae for the features are to be adapted to that effect that a material removal leads to a positive deviation and not to a negative one.

Still further embodiment examples differ from the above-described embodiment examples in that as an ultrasound property there is not used the ultrasound transmission but the ultrasound remission. The transmission ultrasound sensor is then replaced by a corresponding ultrasound remission sensor. In this case an adhesion or crease increases the ultrasound remission, so that the method steps are to be adapted accordingly. A material removal, however, will reduce the ultrasound remission, so that the method steps are to be adapted accordingly.

The invention claimed is:

1. A method for checking a value document of a specified value document type for a presence of at least one irregularity of at least one specified type, in which
   an ultrasound data record is captured, which describes in locally resolved fashion at least one ultrasound property, of the value document;
   a deviation data record is ascertained, which describes in locally resolved fashion a deviation between an ultrasound data record and a model and is ascertained such that the deviation described thereby is minimal with respect to the model, wherein the model comprises a model for location dependence of the at least one ultrasound property of reference value documents of the specified value document type without irregularities of the at least one specified type, wherein the model defines a plurality of model data records differing from each other, which describe the at least one ultrasound property in location-dependent fashion; and
   using the deviation data record, checking whether an indication of an irregularity of the at least one specified type is present on the value document.

2. The method according to claim 1, in which the ultrasound data records respectively include ultrasound data for a number N of places which is specified for the value document type, which data respectively describe the at least one ultrasound property for the respective places, and in which the model data records respectively include model data for the at least one ultrasound property for the specified number N of places and lie in a specified partial region of an N-dimensional space of possible ultrasound data.

3. The method according to claim 2, in which the partial region is specified such that model data records are representable, upon a representation of the ultrasound data record and the model data records as vectors of the same dimension, by a sum of a mean vector and a linear combination of at least five specified partial-region vectors.

4. The method according to claim 3, in which the mean vector and the partial-region vectors are obtainable, or obtained by analysis of reference ultrasound data records for specified reference value documents of the specified value document type without irregularities of the at least one specified type.

5. The method according to claim 4, in which the analysis comprises a main component analysis, wherein a mean value ascertained upon the main component analysis corresponds to the mean vector and the main components ascertained upon the main component analysis correspond to the partial-region vectors.

6. The method according to claim 2, in which the model has a statistical model distribution which describes a probability of the occurrence of model data records.

7. The method according to claim 2, in which at least one feature is ascertained for the deviation data record, and upon checking whether an indication of an irregularity of the at least one specified type is present on the value document the at least one feature is employed, or in which at least two features are ascertained for the deviation data record, and upon checking whether an indication of an irregularity of the at least one specified type is present on the value document the at least two features are employed.

8. The method according to claim 6, in which at least one feature is ascertained for the deviation data record, and upon checking whether an indication of an irregularity of the at least one specified type is present on the value document the at least one feature is employed, or in which at least two features are ascertained for the deviation data record, and upon checking whether an indication of an irregularity of the at least one specified type is present on the value document the at least two features are employed.

9. The method according to claim 7, in which the feature or one of the features describes a probability that the ultrasound data record or the deviation data record or the model data records corresponding to the deviation data record occurs according to the model.

10. The method according to claim 7, in which the feature or one of the features describes a quantity of the deviation described by the deviation data record.

11. The method according to claim 7, in which the feature or one of the features represents a measure for a magnitude of deviations at places at which a difference between ultrasound transmission and model, ascertainable from deviation data of the deviation data record, indicates an irregularity of the at least one specified type.

12. The method according to claim 7, in which the feature or one of the features represents a measure of places, for which deviation data of the deviation data record indicate an irregularity of the at least one specified type, occurring spatially cumulated, and that upon ascertaining the measure also the quantities of deviations are taken into account.

13. The method according to claim 7, in which the feature or one of the features represents a measure for a presence of deviations at places for which deviation data of the deviation data record indicate an irregularity of the at least one specified type, along a line of a specified form.

14. The method according to claim 7, in which upon checking whether an indication of an irregularity of the at least one specified type is present on the value document a classification is carried out by means of a support vector machine, using the at least one feature or the features.

15. The method according to claim 8, in which upon checking whether an indication of an irregularity of the at least one specified type is present on the value document a classification is carried out by means of a support vector machine, using the at least one feature or the features.

16. The method according to claim 1, in which irregularities of the at least one specified type comprise irregularities of the type of an adhesion, and/or irregularities of the crease type.

17. The method according to claim 1, in which irregularities of the at least one specified type comprise irregularities of the type of a material removal.

18. An apparatus for checking a value document of a specified value document type for a presence of at least one irregularity of at least one specified type, having an evaluation device which is configured for executing the method according to claim 1, and in particular for
 capturing an ultrasound data record which describes in locally resolved fashion at least one ultrasound property, an ultrasound transmission, of the value document;
 ascertaining a deviation data record which describes in locally resolved fashion a deviation between the ultrasound data record and a model and is ascertained such that the deviation described thereby is minimal with respect to the model, wherein the model comprises a model for a location dependence of the at least one ultrasound property of reference value documents of the specified value document type without irregularities of the at least one specified type and defines a plurality of model data records differing from each other which describe the at least one ultrasound property in location-dependent fashion; and
 using the deviation data record, checking whether an indication of at least one irregularity of the at least one specified type is present on the value document.

19. The apparatus according to claim 18, which further has an ultrasound sensor for a locally resolved measurement of the at least one ultrasound property of a value document and formation of an ultrasound data record for the value document, and
 in which the evaluation device is coupled to the ultrasound sensor via a signal connection and is configured to capture an ultrasound data record of the ultrasound sensor as an ultrasound data record.

20. A computer program for execution by means of a data processing device, which has program code, upon the execution of which the data processing device executes the method according to claim 1.

21. A data carrier which is readable by means of a data processing device and on which the computer program according to claim 20 is stored.

22. A method for generating ultrasound training data for adapting parameters of a method for checking a value document of a specified value document type for a presence of at least one irregularity of at least one specified type, for adapting parameters of the method according to claim 1, in which for specified reference value documents of the specified value document type there are captured ultrasound data records which respectively describe in locally resolved fashion at least one ultrasound property, an ultrasound transmission, of the respective reference value document, wherein the specified reference value documents do not have an irregularity of the at least one specified type;

at least some of the ultrasound data records are stored as ultrasound training data records;

from at least some of the ultrasound data records there are generated further ultrasound training data records, by changing, for respectively given places, ultrasound data of the ultrasound data record in such a way that the change corresponds to a given irregularity of the at least one specified type, and the further ultrasound training data records are stored; and wherein the parameters of the checking method are adapted using the ultrasound training data records.

23. The method according to claim 22, in which upon the generation of one of the further ultrasound training data records the places are respectively given such that the form and/or the position of the irregularity of the specified type is chosen from a specified set of possible forms or positions.

24. The method according to claim 22, in which upon the generation of one of the further ultrasound training data records, a quantity of the change by the irregularity of the specified type is chosen from a specified region or a specified set.

\* \* \* \* \*